US010049407B2

(12) United States Patent
Bradshaw et al.

(10) Patent No.: US 10,049,407 B2
(45) Date of Patent: *Aug. 14, 2018

(54) DYNAMIC AGGREGATION OF INSURANCE PREMIUMS

(75) Inventors: Paul Bradshaw, London (GB); John Anthony Levin, London (GB); Michael Concannon, Mill Valley, CA (US)

(73) Assignee: QUANIS LICENSING LTD., Ebene Mauritius (MU)

(*) Notice: Subject to any disclaimer, the term of this patent is extended or adjusted under 35 U.S.C. 154(b) by 591 days.

This patent is subject to a terminal disclaimer.

(21) Appl. No.: 12/790,758

(22) Filed: May 28, 2010

(65) Prior Publication Data

US 2011/0004493 A1    Jan. 6, 2011

Related U.S. Application Data

(60) Provisional application No. 61/182,589, filed on May 29, 2009.

(51) Int. Cl.
*G06Q 40/08* (2012.01)
*G06Q 50/24* (2012.01)
*G06Q 20/38* (2012.01)

(52) U.S. Cl.
CPC ........... *G06Q 40/08* (2013.01); *G06Q 20/389* (2013.01); *G06Q 50/24* (2013.01)

(58) Field of Classification Search
CPC .................................................... G06Q 40/08
USPC .......................................................... 705/4
See application file for complete search history.

(56) References Cited

U.S. PATENT DOCUMENTS

| 4,831,693 | A | | 5/1989 | Veith et al. |
| 4,837,693 | A | | 6/1989 | Schotz |
| 5,752,236 | A | | 5/1998 | Sexton et al. |
| 5,839,118 | A | * | 11/1998 | Ryan et al. ................. 705/36 R |
| 5,956,691 | A | | 9/1999 | Powers |
| 6,999,935 | B2 | | 2/2006 | Parankirinathan |
| 7,124,088 | B2 | | 10/2006 | Bauer et al. |
| 7,395,219 | B2 | | 7/2008 | Strech |
| 7,657,447 | B2 | | 2/2010 | Patton |
| 7,742,937 | B2 | | 6/2010 | Cox et al. |
| 8,027,822 | B2 | | 9/2011 | Turgiss et al. |

(Continued)

FOREIGN PATENT DOCUMENTS

| WO | WO-0139090 A1 | 5/2001 |
| WO | WO-2006013425 A2 | 2/2006 |

(Continued)

OTHER PUBLICATIONS

"International Application Serial No. PCT/US10/36750, Search Report dated Jul. 30, 2010", 4 pgs.

(Continued)

*Primary Examiner* — Hao Fu
(74) *Attorney, Agent, or Firm* — Thorpe North & Western (57) ABSTRACT

A method to dynamically aggregate insurance premiums is disclosed. An insurance policy is dynamically adjusted responsive to input data received at a dynamic provisioning system, the adjusting including a calculating of a new premium of the insurance policy. An amount of a payment of the new premium is identified based on preference data received at the dynamic provisioning system. An entity insured by the insurance policy is notified of the amount.

18 Claims, 6 Drawing Sheets

(56) References Cited

U.S. PATENT DOCUMENTS

| | | | |
|---|---|---|---|
| 8,041,636 | B1 | 10/2011 | Hunter et al. |
| 8,073,715 | B1* | 12/2011 | Smith ............................... 705/4 |
| 8,090,592 | B1 | 1/2012 | Goodall et al. |
| 8,180,655 | B1 | 5/2012 | Hopkins, III |
| 2001/0040591 | A1 | 11/2001 | Abbott et al. |
| 2002/0002475 | A1 | 1/2002 | Freedman et al. |
| 2002/0095317 | A1 | 7/2002 | McCabe |
| 2002/0188480 | A1 | 12/2002 | Liebeskind et al. |
| 2003/0018576 | A1 | 1/2003 | Zuckerbrot et al. |
| 2003/0078817 | A1 | 4/2003 | Harrison et al. |
| 2003/0120520 | A1* | 6/2003 | Cumming et al. ............... 705/4 |
| 2003/0158758 | A1 | 8/2003 | Kanazawa et al. |
| 2003/0187693 | A1 | 10/2003 | Oka et al. |
| 2004/0030587 | A1* | 2/2004 | Danico et al. ..................... 705/4 |
| 2004/0059608 | A1 | 3/2004 | Gore et al. |
| 2004/0103012 | A1 | 5/2004 | Nussbaum et al. |
| 2004/0122770 | A1 | 6/2004 | Craig et al. |
| 2004/0148201 | A1 | 7/2004 | Smith et al. |
| 2004/0153362 | A1 | 8/2004 | Bauer et al. |
| 2004/0267651 | A1 | 12/2004 | Jenson et al. |
| 2005/0071204 | A1 | 3/2005 | Parankirinathan |
| 2005/0267785 | A1 | 12/2005 | Parankirinathan et al. |
| 2006/0100912 | A1 | 5/2006 | Kumar et al. |
| 2006/0136273 | A1 | 6/2006 | Zizzamia et al. |
| 2006/0184387 | A1 | 8/2006 | Richardson et al. |
| 2007/0255601 | A1 | 11/2007 | Heydon et al. |
| 2008/0033767 | A1* | 2/2008 | Brown .............................. 705/4 |
| 2008/0065426 | A1 | 3/2008 | Ziade et al. |
| 2008/0109333 | A1* | 5/2008 | Camp et al. .................... 705/35 |
| 2008/0126139 | A1 | 5/2008 | Prendergast et al. |
| 2008/0154651 | A1 | 6/2008 | Kenefick et al. |
| 2008/0183636 | A1 | 7/2008 | Walsh et al. |
| 2009/0024420 | A1 | 1/2009 | Winkler |
| 2009/0037229 | A1 | 2/2009 | Perez Munoz et al. |
| 2009/0112634 | A1 | 4/2009 | Koziol |
| 2009/0132299 | A1* | 5/2009 | Patton .............................. 705/4 |
| 2010/0088124 | A1 | 4/2010 | Diefendorf et al. |
| 2010/0131303 | A1 | 5/2010 | Collopy et al. |
| 2010/0131305 | A1 | 5/2010 | Collopy et al. |
| 2010/0312584 | A1 | 12/2010 | Bradshaw et al. |
| 2011/0004492 | A1 | 1/2011 | Bradshaw et al. |

FOREIGN PATENT DOCUMENTS

| | | |
|---|---|---|
| WO | WO-2006031747 A2 | 3/2006 |
| WO | WO-2010/138932 A1 | 12/2010 |

OTHER PUBLICATIONS

"International Application Serial No. PCT/US10/36750, Written Opinion dated Jul. 30, 2010", 6 pgs.

"U.S. Appl. No. 12/790,750, Final Office Action dated Jun. 5, 2012", 12 pgs.

"U.S. Appl. No. 12/790,750, Non Final Office Action dated Nov. 14, 2011", 11 pgs.

"U.S. Appl. No. 12/790,753 , Response dated May 31, 2012 to Non Final Office Action dated Jan. 31, 2012", 15 pgs.

"U.S. Appl. No. 12/790,753, Non Final Office Action dated Jan. 31, 2012", 22 pgs.

"Australian Application Serial No. 2010253917, Office Action dated Dec. 20, 2011", 1 pg.

"Australian Application Serial No. 2010253917, Response dated Jan. 3, 2012 to Office Action dated Dec. 20, 2011", 1 pg.

"International Application Serial No. PCT/US2010/036750, International Preliminary Report on Patentability dated Jul. 6, 2012", 18 pgs.

Furhaupter, Rainer, "Adjustment in a fully-funded system", http://www.actuaries.org/EVENTS/Congresses/Cancun/health subject/health_28_40_49_furhaupter.pdf, (Mar. 19, 2002), 25.

Kominski, Gerald, "Medicare's Use of Risk Adjustment", National Health Policy Forum, http://www.nhpf.org/library/background-papers/BP_RiskAdjustMedicare_08-21-07.pdf, (Aug. 21, 2007), 17.

"U.S. Appl. No. 12/790,750, Response dated Sep. 24, 2012 to Final Office Action dated Jun. 5, 2012", 10 pgs.

"U.S. Appl. No. 12/790,753 , Response dated Feb. 11, 2013 to Final Office Action dated Oct. 11, 2012", 22 pgs.

"U.S. Appl. No. 12/790,753, Final Office Action dated Oct. 11, 2012", 26 pgs.

"U.S. Appl. No. 12/790,750, Examiner Interview Summary dated Sep. 12, 2014", 3 pgs.

"U.S. Appl. No. 12/790,750, Final Office Action dated May 1, 2015", 17 pgs.

"U.S. Appl. No. 12/790,750, Final Office Action dated Dec. 8, 2014", 14 pgs.

"U.S. Appl. No. 12/790,750, Non Final Office Action dated Jun. 11, 2014", 15 pgs.

"U.S. Appl. No. 12/790,750, Response dated Mar. 9, 2015 to Non Final Office Action dated Dec. 8, 2014", 37 pgs.

"U.S. Appl. No. 12/790,750, Response dated Mar. 14, 2012 to Non Final Office Action dated Nov. 14, 2011", 12 pgs.

"U.S. Appl. No. 12/790,750, Response dated Sep. 19, 2014 to Non-Final Office Action dated Jun. 11, 2014", 17 pgs.

"U.S. Appl. No. 12/790,753, Non Final Office Action dated Oct. 1, 2014", 32 pgs.

"U.S. Appl. No. 12/790,753, Response dated Feb. 2, 2015 to Non Final Office Action dated Oct. 1, 2014", 43 pgs.

"European Application Serial No. 10781353.7 Response dated Feb. 23, 2015 to Office Action dated Jul. 25, 2014", 16 pgs.

"European Application Serial No. 10781353.7, Extended European Search Report dated Jul. 25, 2014", 7 pgs.

"European Application Serial No. 10781353.7, Response dated Aug. 8, 2012", 10 pgs.

"International Application Serial No. PCT/US2010/036750, Response to Written Opinion dated Mar. 29, 2011", 9 pgs.

"Statement in Accordance With the Notice From the European Patent Office dated Oct. 1, 2007 Concerning Business Methods", Epc / Erklaerung Gemaess Der Mitteilung Des Europaeischen Patentamts Vom Oct. 1, 2007 Ueber Geschaeftsmethoden—Epu / Declaration Conformement Au Communique De L'office Europ, (Nov. 1, 2007), 592-593.

"U.S. Appl. No. 12/790,750, Response dated Sep. 1, 2015 to Final Office Action dated May 1, 2015", 32 pgs.

"U.S. Appl. No. 12/790,753, Final Office Action dated May 21, 2015", 30 pgs.

"U.S. Appl. No. 12/790,753, Response dated Aug. 21, 2015 to Final Office Action dated May 21, 2015", 27 pgs.

"Australian Application Serial No. 2010253917, First Examiner Report dated Nov. 24, 2011", 3 pgs.

"U.S. Appl. No. 12/790,750, Appeal Brief dated Mar. 23, 2017", 33 pgs.

"U.S. Appl. No. 12/790,750, Final Office Action dated May 26, 2017", 13 pgs.

"U.S. Appl. No. 12/790,750, Final Office Action dated Dec. 28, 2016", 13 pgs.

"U.S. Appl. No. 12/790,750, Non Final Office Action dated May 16, 2016", 20 pgs.

"U.S. Appl. No. 12/790,750, Response dated Sep. 26, 2017 to Final Office Action dated May 26, 2017", 13 pgs.

"U.S. Appl. No. 12/790,750, Response dated Oct. 17, 2016 to Non Final Office Action dated May 16, 2016", 24 pgs.

"U.S. Appl. No. 12/790,753, Final Office Action dated Jan. 5, 2017", 35 pgs.

"U.S. Appl. No. 12/790,753, Non Final Office Action dated Jun. 10, 2016", 38 pgs.

"U.S. Appl. No. 12/790,753, Response dated Nov. 10, 2016 to Non Final Office Action dated Jun. 10, 2016", 29 pgs.

"Australian Application Serial No. 2010253917, Response dated Nov. 15, 2016 to First Examiner Report dated Nov. 24, 2015", 24 pgs.

"Metadata", [Online]. Retrieved from the Internet: http://www.oxforddictionaries.com/us/definition/american_english/metadata, 10 pgs.

* cited by examiner

DYNAMIC AGGREGATION OF INSURANCE PREMIUMS

CROSS-REFERENCE TO RELATED APPLICATIONS

This application claims the priority benefit of U.S. Provisional Application No. 61/182,589, entitled, "Variable Life Protection Base on Dynamic Inputs," filed May 29, 2009, which is hereby incorporated herein by reference in its entirety.

BACKGROUND

Insurance is typically viewed as a form of risk management, in terms of which there is a transfer of risk from an insured party to an insurer party in exchange for a premium. An insurer may be a corporation selling the insurance, while an insured (e.g., the policy holder or owner) is typically a person or an entity that is buying the insurance. An insurer charges the insured a premium, which is typically a once-off or recurring monetary payment from the insured to the insurer in exchange for the assumption of the risk by the insurer. There are many types of insurance, such as auto insurance, home insurance, health insurance, disability insurance, casualty insurance, life insurance, and credit insurance, to name but a few.

Life insurance (or assurance) is typically provided in terms of a contract between a policy owner and an insurer. The contract may obligate the insurer to pay a sum of money to a beneficiary specified by the policy holder upon the policy holder's death, terminal illness or catastrophic event.

The insurer typically calculates policy prices using mortality tables (i.e., statistically-based tables showing expected annual mortality rates). Main variables in mortality tables have traditionally been age, gender and use of tobacco.

Life insurance is often provided in two basic classes, namely temporary life insurance or permanent life insurance. Temporary life insurance provides coverage for a specified term of years for a specified premium, while permanent life insurance remains in force until the relevant policy matures or pays out.

U.S. Pat. No. 7,395,219 describes an "insurance on demand" transaction management system that implements an intermittent risk exposure liability insurance method. The method involves establishing an Internet business site enabled for communication between insurers and insured. Insureds are enrolled in intermittent risk exposure liability insurance policies. These policies provide a variable insurance premium rate depending upon an intermittent use of an insured article (e.g., a motor vehicle). The start and completion times of each intermittent use of the insured article are logged on the Internet business site by the insured. These start and completion times are verified. Premium insurance rates are applied and billed in accordance with the verified log start and completion times of use.

U.S. Pat. No. 5,839,118 describes linking an external computer with a system of an insurance carrier and a system of an independent lending institution to determine an optimal premium structure for a variable life insurance product, using a portion of a policy owner's money and a lending institution loan to finance a premium. The system provides for the tracking of several variable life insurance policy cash values to ensure each individual policy cash value is adequate for collateral purposes.

BRIEF DESCRIPTION OF DRAWINGS

Some embodiments are illustrated by way of example and not limited in the figures of the accompanying drawings in which.

DETAILED DESCRIPTION

In the following description, for purposes of explanation, numerous specific details are set forth in order to provide a thorough understanding of some example embodiments. It will be evident, however, to one skilled in the art that the subject matter of this disclosure may be practiced without these specific details.

As used herein, the terms "person," "individual," "entity," or "customer" are used interchangeably to refer to a party (e.g., an insured or an insurer) that interacts with a dynamic provisioning system.

Example embodiments include systems and methods for providing life assurance protection based on changes in individual and environmental characteristics that are partly predefined by the insured party (e.g., a customer). It should be noted that embodiments of the present invention may be utilized to provide other forms of insurance protection.

Figure 1:
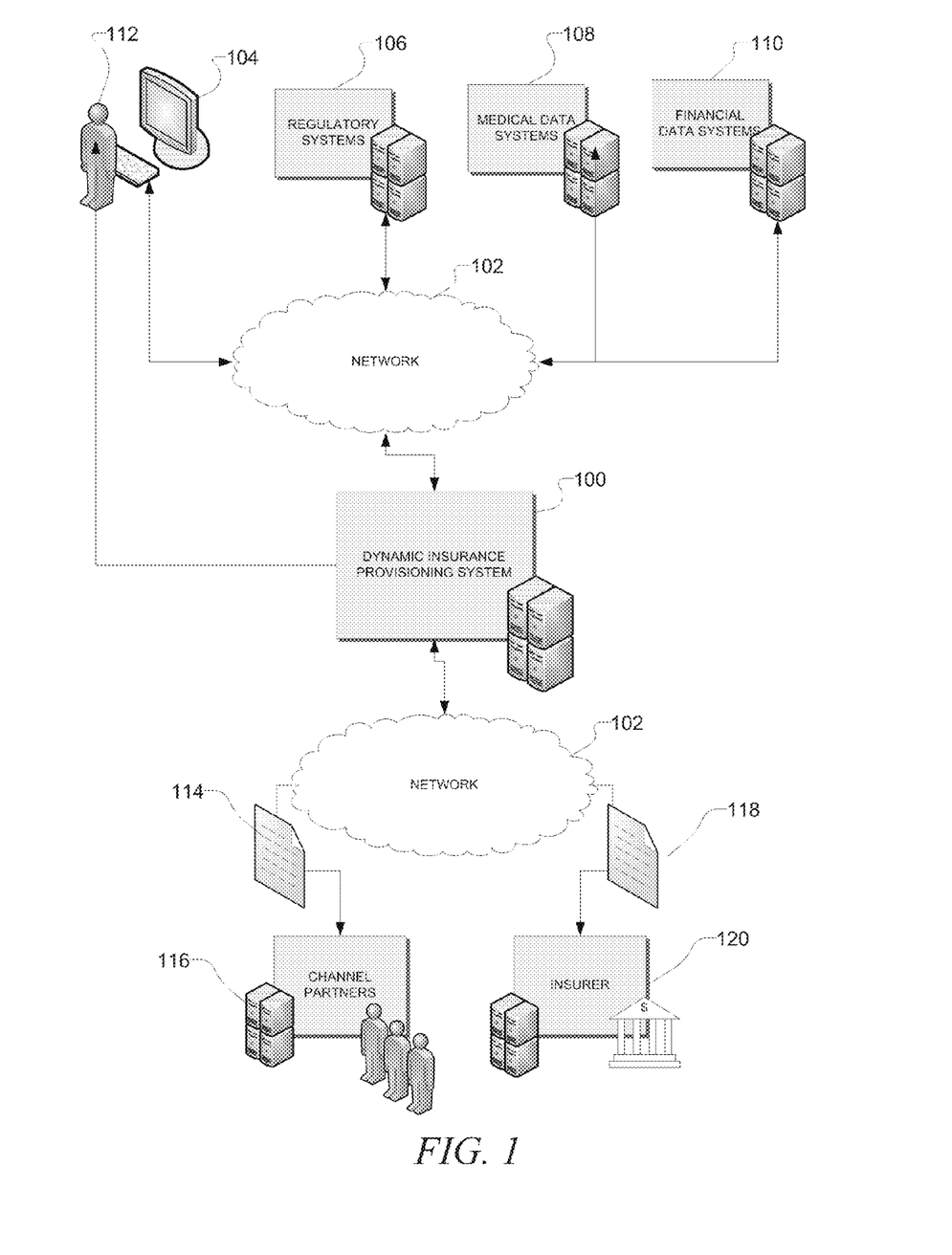
FIG. 1 is a schematic diagram illustrating an insurance provisioning environment within a dynamic insurance provisioning system, according to an example embodiment.

FIG. 1 is a schematic diagram illustrating an insurance provisioning environment within which a dynamic insurance provisioning system 100 may be deployed, according to an example embodiment. The dynamic insurance provisioning system 100 is shown to be communicatively coupled by a network 102 to one or more information sources. The information sources may include one or more network access devices (e.g., a personal computer system 104), regulatory computer systems 106, medical data systems 108, and financial data systems 110. The dynamic insurance provisioning system 100 may receive inputs (or input data) from one or more sources. The inputs may include entity inputs (or entity input data), environmental inputs (or environmental input data), customer preference inputs (or customer preference data or customer preference input data or customer preferences), regulatory inputs (or regulatory input data), medical inputs (or medical input data), market inputs (or market input data), or other inputs.

In various embodiments, the dynamic insurance provisioning system 100 may update previously received or stored input data to determine whether a risk (e.g., an underwriting risk) associated with providing an insurance policy has changed. Based on this determination, the dynamic insurance provisioning system 100 may recalculate a coverage amount, a coverage time period, or a premium of the insurance policy. In various embodiments, the dynamic insurance provisioning system 100 may initiate the updating in response to receiving a preference of an insured entity or an insuring entity regarding when (e.g., a date or a time) or how often (e.g., a frequency) a coverage amount, a coverage time period, or a premium of the insurance policy is to be updated. The dynamic insurance provisioning system 100 may amend the insurance policy based on the updating.

For example, an entity (e.g., a person 112 or a corporation (e.g., via an agent)) may use the personal computer system 104 or other network access device (e.g., a mobile communication device, such as a mobile phone, personal digital assistant, netbook, e-reader, and so on) to provide entity inputs (also called entity input data) or customer preference inputs to the dynamic insurance provisioning system 100. In an example embodiment, an entity may be a corporation that is acting (e.g., via an agent) on behalf of itself or on behalf of one or more individuals. The entity may provide the entity inputs or customer preference input data using software running on the client system that accesses the dynamic insurance provisioning system 100.

The dynamic insurance provisioning system 100 may receive the input data (e.g., via a publish/subscribe system or by querying interfaces (e.g., application program interfaces (APIs))). An entity may also provide entity inputs or customer preference data using an out-of-band communication channel (e.g., a voice call). The dynamic insurance provisioning system 100 may further receive (e.g., via the publish/subscribe system or querying interfaces) regulatory inputs in the form of regulatory information from the regulatory computer system 106, medical information (e.g., pertaining to the person 112 or to a group of people) from the medical data systems 108, and financial data (e.g., wealth data for the person 112 or market data pertaining to one or more markets) from the financial data systems 110.

The dynamic insurance provisioning system 100 may store the entity inputs, the customer preference data, the regulator information, the market data, or other data in storage (e.g., a database, file system, or memory; not shown). The dynamic insurance provisioning system 100 may make a decision whether to store the customer preference data based on the received entity input data. The dynamic insurance provisioning system 100 may access the data in the storage (e.g., using an operating system command, an API, or a query) for further processing or analysis.

The dynamic insurance provisioning system 100 is furthermore shown, in FIG. 1, to be communicatively coupled via the network 102 (e.g., the Internet) to channel partner computer systems 116 and an insurer computer system 120. The channel partner computer systems 116 may be associated with the various channel partners, such as brokers, agents and financial advisors that broker and sell insurance products of an insurer associated with the insurer computer system 120. The dynamic insurance provisioning system 100, as will be described in detail below, uses the various inputs from the systems 104-110 to dynamically calculate period commissions 114, which are communicated to the channel partner computer systems 116 (or to bank accounts associated with the channel partners), and a period premium 118, which is communicated to the insurer computer system 120 (or to a bank account associated with the insurer). A period premium is one of a series of premiums that may be different from another one of the series of premiums. For example, with respect to an insurance policy having an adjustable premium, the amount of the premium prior to an adjustment of the premium may be considered to be a first period premium and the amount of the premium after the adjustment may be considered to be a second period premium. As another example, the amount of a premium prior to a renewal of an insurance policy may be considered to be a first period premium and the amount of the premium after the renewal of the policy may be considered to be a second period premium. Similarly, a period commission is one of a series of commissions that may be different from another one of the series of commissions. A period commission may be associated with a period premium. For example, a period commission may be provided to a channel partner upon a renewal of an insurance policy.

Figure 2:
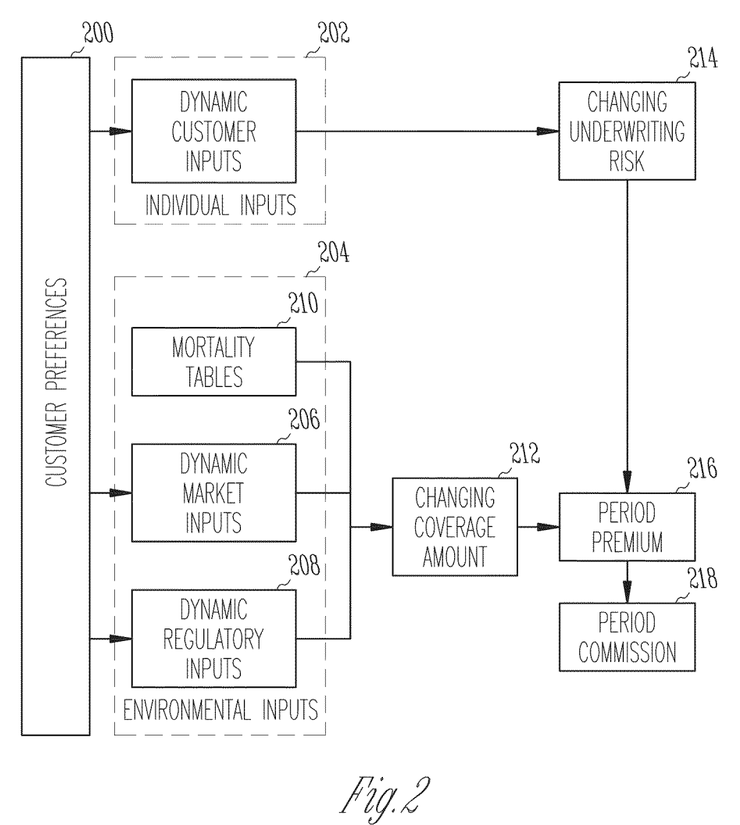
FIG. 2 is a block diagram providing a high-level representation of relationships between information components of the example system, as may be processed by example methods.

FIG. 2 is a block diagram providing a high-level representation of relationships between information components of the example dynamic insurance provisioning system 100, as may be processed by example methods. A policy is recalculated or reissued based on customer preferences 200 that define a specified time interval and a trigger threshold for accepting input changes, which in turn generate a trigger to change the underwriting risk or coverage amount.

Entity inputs 202 may include one or more inputs pertaining to (or specific to) a person (e.g., individual inputs or individual input data), a corporation (e.g., corporation inputs or corporation input data), or another entity. Examples of corporation inputs may include values corresponding to a corporation's size (e.g., number of employees), geographic location, or business focus. Examples of individual inputs may include values corresponding to a person's health status, biometric inputs (e.g., sensed physiological or behavioral characteristics, such as fingerprint, facial, iris, gait, voice, or other characteristics), marital status, location, or age.

Environmental inputs 204 may include market inputs 206 (e.g., to perform a market valuation of a customer's net worth), regulatory inputs 208 (e.g., regulatory changes to determine individual liability such as inheritance/estate tax), and mortality table 210 (e.g., mortality data that refactors the underlying risk; the refactoring may include, for example, incorporating population mortality data).

Data inputs (or inputs), including entity inputs 202 and environmental inputs 204, may be captured through a combination of manual and automatic data feeds, such as through a biometric sensor, a manually entered cholesterol value, or an automatic updating of the customer's net worth. For example, inputs may be captured through system integration with an Internet-based portfolio administration service (e.g., a "wrap" platform, such as Aviva's Wrap and Sipp Platform or AXA's Elevate wrap platform). The Internet-based portfolio administration service may be one of the financial data systems 110 of FIG. 1.

If a change in input causes a change in coverage amount 212 or underwriting risk 214, then the dynamic insurance provisioning system 100 recalculates the period premium amount 216. A new premium amount 216 triggers a change in the period commissions 218 paid, for example, as trail commission that can be calculated daily and paid monthly to the agent/distribution channel.

By having the coverage amount based on independently verifiable external variables, such as customer's net worth or current inheritance/estate tax calculations, the adverse/anti-selection risk is significantly reduced, thus reducing the underwriting burden, speed of issuance, and overall cost.

Further details of the example information components shown in FIG. 2 are now discussed.

Customer preferences data 200 may be categorized as personal attributes and product preferences. Personal attributes include preferences for capturing personal information, such as a cell phone broadcast or a self-report for determining country location. Product preferences may include time period and threshold triggers to determine when a particular input, such as net worth, is considered for recalculation of underwriting risk or coverage amount. Time period is based on time intervals, such as real time, daily, weekly, monthly, quarterly, or annual. Thresholds may be based on either absolute or percentage changes of input.

Figure 3:
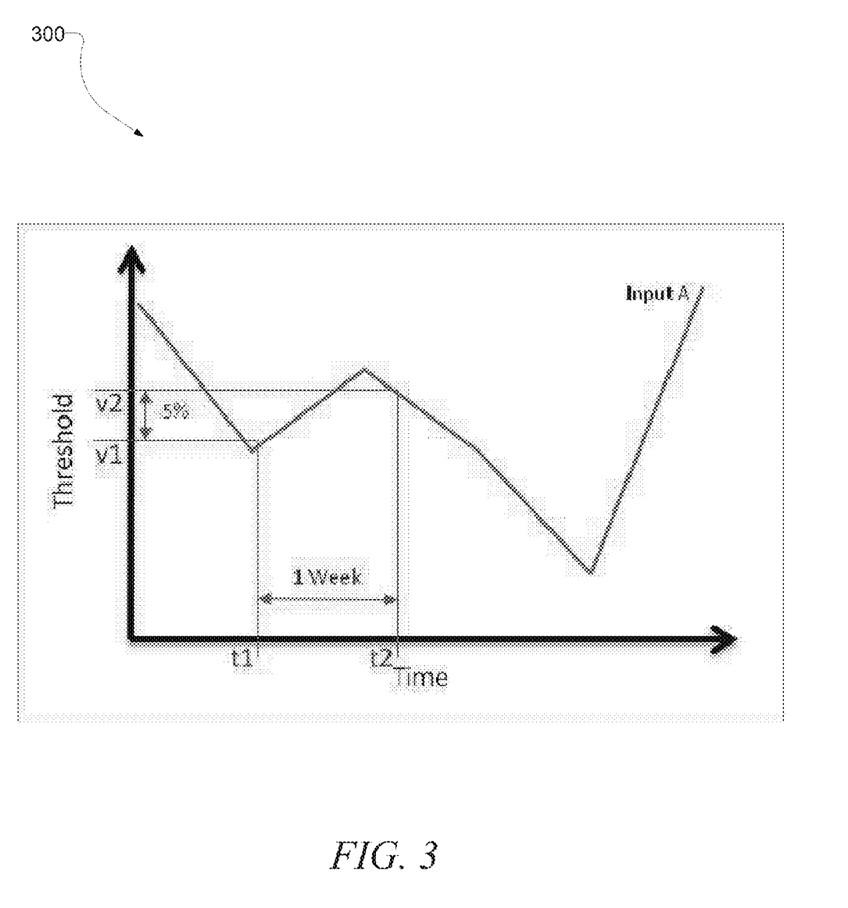
FIG. 3 is a graph that provides an example for a scenario in which a customer preference for sampling net worth (Input A) is set to a time period of 1 week (t2−t1=1 week) and a trigger threshold is set to 10%.

FIG. 3 shows a graph 300 that provides an example of a scenario in which a customer preference for sampling net worth (Input A) is set to time period of 1 week (t2−t1=1 week) and a trigger threshold is set to 10%. In the graphed example, Input A would not trigger a recalculation of coverage amount because the value of Input A only changed 5% over the time period. In other scenarios, multiple triggers may be associated with each one of multiple inputs, including entity inputs 202 or environmental inputs 204.

Referring back to FIG. 2, entity inputs 202 may be captured though automatic and manual data uploads. The entity inputs may include such information as biometric data through biometric sensors, health status change through physician statements or electronic heath records, weight, body mass index (BMI), level of fitness, cholesterol, or marital status. Entity inputs 202 primarily drive underwriting risk, although inputs such as marital status may combine with environmental inputs 204 to determine coverage amount (e.g., all things being equal, coverage amount for an unmarried customer will be different than coverage amount for a married customer because inheritance tax (IHT) liability is different).

The entity inputs 202 may be independently (or externally) verifiable. The dynamic insurance provisioning system 100 may use a weighting mechanism to assign weights to entity inputs 202 according to an extent that such entity inputs 202 are independently verifiable. For example, the dynamic insurance provisioning system 100 may assign weights having high values to entity inputs 202 received automatically through a biometric device (indicating a relatively great level of external verifiability) and weights having low values to entity inputs 202 received as a result of manual inputs by the person 112 or other entity (indicating a relatively low level of external verifiability). The dynamic insurance provisioning system 100 may then use the weights when performing any one of various calculations, including, for example, a calculation of underwriting risk. The dynamic insurance provisioning system 100 may consider entity inputs 202 to be generally less independently verifiable than environmental inputs 204 and may therefore typically assign weights having lower values to entity inputs 202 than to environmental inputs 204.

Environmental inputs 204 may be data inputs that are not specific to an entity but nevertheless impact both coverage amount 212 and underwriting risk 214. The environmental inputs may be external to the entity inputs 202. For example, environmental inputs may come from an Internet-based portfolio administration service that tracks market changes or regulatory changes in IHT calculations that impact coverage amount 212. The market changes or regulatory changes may be categorized as environmental inputs 204 because they are not specific to an entity. Furthermore, market changes or regulatory changes may be external to entity inputs 202, but may include data that affects the entity inputs 202 (e.g., a customer's investment portfolio).

It will also be appreciated that mortality tables, which may contain population mortality data, may not be specific to an entity. Mortality tables may be external to entity inputs 202 (e.g., automatically loaded as they are published by an external source). Mortality tables may impact the customer's underwriting risk 214, resulting in a recalculation of the period premium 216.

Environmental inputs 204 may be independently verifiable. The dynamic insurance provisioning system 100 may use a weighting mechanism like the one described above with respect to entity inputs 202 to assign weights to the environmental inputs 204. The dynamic insurance provisioning system 100 may then use the weights when performing any one of various calculations, including, for example, a calculation of underwriting risk. The dynamic insurance provisioning system 100 may consider environmental inputs 204 to be generally more independently verifiable than entity inputs 202 and may therefore typically assign weights having higher values to environmental inputs 204 than to entity inputs 202.

A customer's underwriting risk 214 may be calculated in real-time as entity inputs 202 (e.g., customer inputs) or environmental inputs 204 are received. Changes to mortality data 210 may be manually or automatically fed into the system. At the time of initial underwriting, the customer may be provided with an option to select underwriting bands in excess of an initial coverage amount. These bands may determine the medical evidence that the customer should supply to support a coverage amount 212 within that band. Such bands may become "binding bands" at the time of policy issuance, and may allow the coverage amount 212 to flex up to that amount without requiring additional medical underwriting. For example, a customer's initial coverage may be set at 1 million Euros and may require the customer to undergo a qualifying process, such as completing a simple blood and urine test. At time of medical underwriting, the customer may choose to select a binding band of up to 5 million Euros and therefore may have to undergo an additional qualifying process, such as an electrocardiogram (EKG) or a treadmill test. This medical information may be gathered, processed, and underwritten by an underwriting information coordination (UIC) module (to be described in further detail below) and the binding band (or range) may be written into the customer's record within a dynamic risk assessor (DRA) module (also to be described in further detail below).

The coverage amount 212 for the customer may be the policy face amount for the time period. It may be recalculated based on changes in environmental inputs 204 and entity inputs 202. The coverage amount 212 may be required or optional (e.g., recommended). For example, the coverage amount 212 may be required if the customer is obligated by a third party to carry an amount of insurance that corresponds to the coverage amount 212. For example, the coverage amount 212 may be required if a mortgagor of a property contractually obligates a mortgagee to maintain an amount of insurance coverage on the property that is equal to the coverage amount 212. Alternatively, the coverage amount may be recommended if the customer is not obligated to a third party to maintain the coverage amount 212. For example, the coverage amount 212 may be recommended if the customer is obtaining or managing a life insurance for no other reason than for his own peace of mind. The coverage amount 212 may increase or decrease. If the coverage amount 212 is recommended, the customer may be given an option to accept the recommended amount.

The period for premium calculation may be determined by the customer preferences 200. A premium calculator module, described in further detail below, receives inputs (e.g., the underwriting risk 214 and the coverage amount 212) to determine a period premium 216. The period premiums 216 can be aggregated over a period to consolidate billing. For example, a customer may choose to set a recalculation time interval (or frequency) equal to daily. While a daily premium is calculated, the total for the month is calculated and customer is invoiced at the end of the month. The recalculation frequency may, in turn, affect a frequency at which the dynamic insurance provisioning system 100 initiates a receiving of updates of input data.

The amount of commission 218 paid to distributors (e.g., agents, brokers, or independent financial advisors (IFAs)) may be set as a function of premium earned. The commission 218 may be earned on a time interval basis and from that basis a variable trail-based commission may be paid. A trail commission tracker component, described in further detail below, tracks and disburses commissions 218 to the appropriate distribution stakeholders. Commission 218 may be paid on the sum of one or more period premiums 216.

Figure 4:
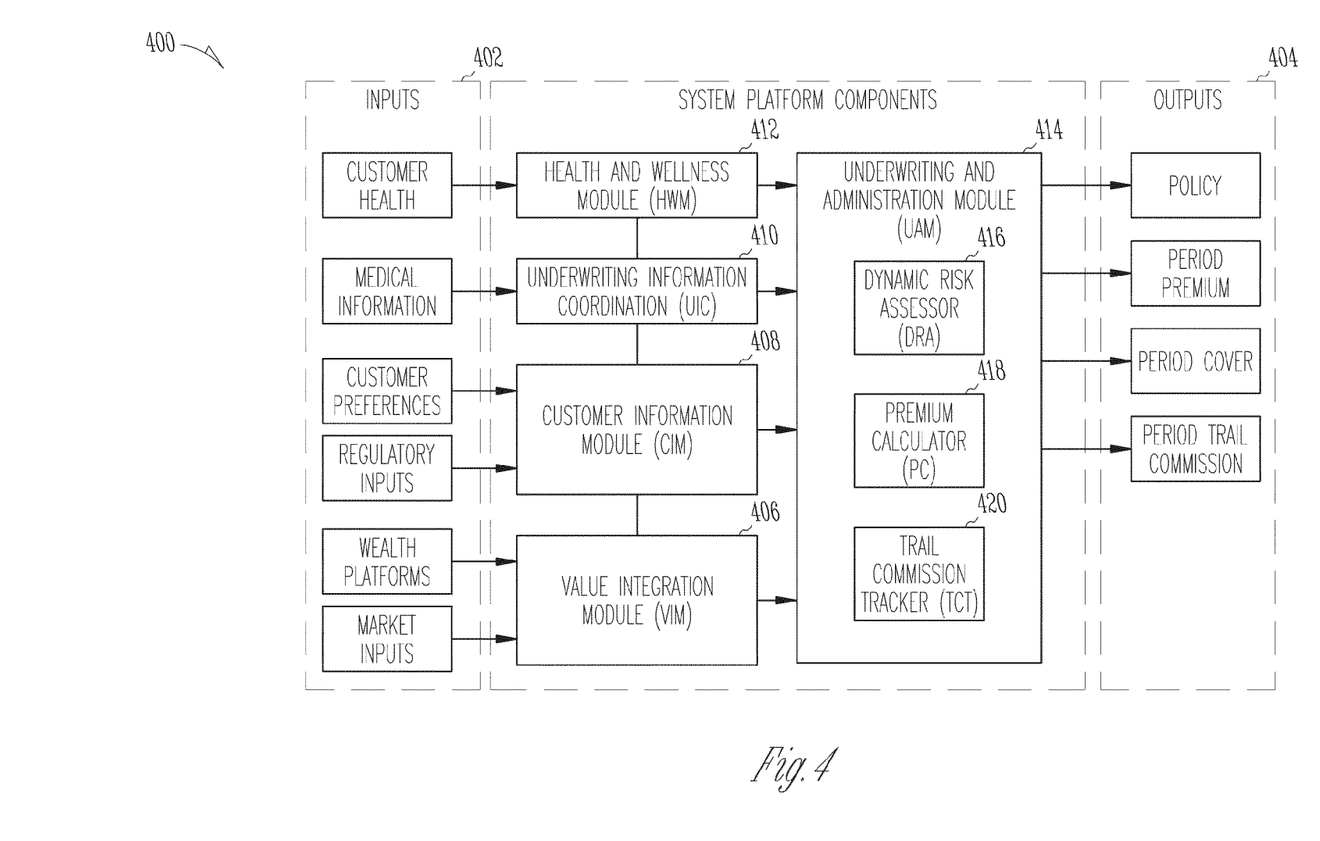
FIG. 4 is a block diagram illustrating the architecture of a dynamic insurance provisioning system, according to an example embodiment.

FIG. 4 is a block diagram illustrating the architecture of a dynamic insurance provisioning system 400, according to an example embodiment. The system 400 is shown to comprise a number of modules that receive inputs 402 (e.g., the inputs 202 and 204 discussed above with reference to FIG. 2) and interact with each other to provide outputs 404 (e.g., a policy, premium, period cover, or commission amount). The individual components of the system 400 are now discussed.

A value integration (VI) module 406 builds, tracks, and verifies the customer's net worth. The VI module 406 includes a manual data entry interface and automatic data integration component (not shown) for gathering and monitoring the customer's total net worth. The data integration component integrates with third-party systems and information feeds to determine the value of the customer's portfolio. This integration channel uses a multi-channel (e.g., HyperText Transfer Protocol (HTTP), HyperText Transfer Protocol Secure (HTTPS), Web Service, or File Transfer Protocol (FTP)) architecture to automatically receive updates of the value of all classes of assets such as stocks, bonds, warrants, annuities, pensions, art, collectibles and property. For assets not automatically updatable, a manual data entry system, using HTTPS, is used to capture asset value. Customers and system users have access to view and update assets or asset values based on system controlled workflow and approval. For each asset an independent valuation attribute is set and a process for updating and validating values is set.

A customer information (CI) module 408 captures customer preferences (e.g., attribute and product preferences), customer information such as living location, and marital status, and regulatory information, such as IHT rules. Customer preferences for medical underwriting bands are specified in the CI module 408, and requests are made to an underwriting information coordination (UIC) module 410 to schedule examinations, if a determination is made that the customer should provide additional medical information based on a limit of the binding band being reached. Data are updated in the CI module 408 through manual updates using a web browser, or auto data feeds such as the customer's cell phone location signal or third party feeds. The CI module 408 may also specify how much a premium or coverage amount can change without triggering the need for the customer to accept or reject the change.

An underwriting information coordination (UIC) module 410 determines and gathers information requirements to support manual and automatic underwriting decision making. The UIC module 410 collects customer information, diagnoses medical information requirements based on the product and customer preferences set, schedules the examination or collection of information, collects the medical information, and provides the information to an underwriting and administration (UA) module 414. The medical underwriting bands are presented to the customer at a time of scheduling through the CI module 408, allowing for the customer to opt-in for a higher ceiling in the policy binding band to accommodate for greater flex (or range) in coverage amount.

A health and wellness (HW) module 412 provides functionality to measure, monitor and facilitate positive health for the customer. For example, the HW module 412 receives manual and automatic data feeds on a customer's weight, BMI, level of fitness, cholesterol, or smoking habits. The HW module 412 has functionality for requisitioning and managing physician statements or electronic heath records.

The HW module 412 also contains an online survey administration tool for health risk assessment (HRA), and a time-based data model to track and report on changes in customer health. Each information element is attributed with an independently verified source flag and system for updating if independently verifiable. In one instance, each element may be associated with metadata that includes an indicator of whether the information element has been independently verified or an identifier of a system that has performed (or is capable of performing) independent verification of the information element. For example, the HW module 412 may receive entity input data related to a level of fitness of an insured entity (e.g., via the online survey administration tool). Based on a determination that the entity input data has not been independently verified, the HW module 412 may select a source of additional input data. The selection may be based on an ability of the source to provide input data that can be used to independently verify the entity input data (e.g., a source capable of providing EKG or a biometric input data to verify a level of fitness). The HW module 412 may associate metadata with an information element (e.g., the level of fitness of the insured entity) that indicates whether the information has been independently verified. The HW module 412 contains tools and functionality to enable an insurer to interact with a customer to help manage his/her health. The HW module 412 may share the same customer presentation layer as the CI module 408.

An underwriting and administration (UA) module 414 takes real-time data inputs from the other system modules to calculate risk, premium and commission amounts. The UA module 414 generates a new or amended policy, such as new premium, period cover, or commission amounts for a defined time period. The UA module 414 comprises a database and application layer.

A dynamic risk assessment (DRA) component 416 receives inputs (e.g., updates previously received inputs) and contains business logic for determining if a premium calculation or recalculation is necessary and possible based on changes in the customer's risk profile. Based on preset tolerances or thresholds, if a change in one or more input variables such as smoker status, health status, travel/residency, avocation/hazardous pursuits occurs and is within the binding bank, the DRA component 416 passes the appropriate value to a premium calculation (PC) component 418.

Based on input from the DRA component 416, the PC component 418 may perform a calculation of the premium, including a calculation of a period premium or an aggregating of the premium over a period of time. The PC component 418 may calculate one or more amounts of one or more payments of the premium based on input data, including entity input data, environmental input data, or customer preference data. For example, the PC component 418 may determine that an entity should pay the premium in a single payment or in multiple payments based on input data received from a wrap platform. Additionally, the PC component 418 may determine that entity should make payments at one or more specific dates, over a specific time period, or with a specific frequency based on customer preference data (e.g., preferences of an insured entity or an insuring entity). The PC component 418 may perform the calculation in real-time. An illustration of a calculated premium for a joint life policy is provided below.

| | |
|---|---|
| Step 1 | The system calculates the current age based on the coverage start date. $$t_{Age} = \frac{d_{CoverStart} - d_{Birthday}}{365.25}$$ |
| Step 2 | The PC component 418 identifies the rate tables based on Gender, Health and Smoking Status. $T_{Preferred} = f(\text{gender, health, smoking})$ |
| Step 3 | The PC component 418 selects the mortality rate table for the person given the age at the beginning of the coverage and the current year. $q_{Mortality} = f(t_{Age}, t_{Year})$ Note 1: The mortality rate table may be organized such that look ups are based on the age at the start of coverage and the current year as of the calculation. For example, a person being born on Jul. 14, 1971, starting coverage on Dec. 1, 2008, being in Good health, and having given up smoking would have the following mortality rates: <br><br> Year   Mortality Rate <br> 0   0.2976660835 <br> 1   0.3562437660 <br> 2   0.4311634821 <br> 3   0.5129592493 <br> 4   0.6037844779 <br><br> Note 2: The mortality rate will be interpolated over the user defined Time Period to provide a Period value |
| Step 4 | The system calculates the life rate based on the mortality Rate and the Health Loading Factor. $r_{Life} = q_{Mortality} * (1 + f_{HealthLoading})$ |
| Step 5 | If there is a joint life, the system calculates the joint life first rate based on the two individual rates. $$r_{JLF} = 1000 * \left( \frac{r_{Life1} + r_{Life2}}{1000} - \frac{r_{Life1} * r_{Life2}}{1000^2} \right)$$ |
| Step 6 | The system calculates the core price as follows: $$p_{Core} = \frac{r_{Life1} * A_{Life1}}{1000} + \frac{r_{Life2} * A_{Life2}}{1000} + \frac{r_{JLF} * A_{Life\ Joint}}{1000} + c_{Policy} + c_{Trust}$$ $c_{Policy} = c_n(1+i)^n + c_o$ $c_{Trust} = c_n(1+i)^n + c_o$ <br> Note 1: The Core Price is calculated on a yearly basis and can be interpolated for a user defined Time Period <br> Note 2: The Core Price is based on the mortality rate for each life, the assured value, and the cost of the policy. <br> Note 3: The cost of both policy and trust are based on the compound Time Period cost at Time Period X. If one was to compute the cost given the duration the future value of the cost is computed as follows: $$c_{Total} = c * \left[ \frac{(1+i)^n - 1}{i} \right] + c_o$$ |
| Step 7 | The system calculates Travel/Residency Loading price: $$p_{TRL} = \frac{r_{TRLoading1} * A_{Life1}}{1000} + \frac{r_{TRLoading2} * A_{Life2}}{1000}$$ Note 1: The loading factors are further based on the number of periods the loading factor is active for. |
| Step 8 | The System Calculates the Avocation/Hazardous Pursuits Loading Price: $$p_{AHP} = \frac{r_{AHPLoading1} * A_{Life1}}{1000} + \frac{r_{AHPLoading2} * A_{Life2}}{1000}$$ Note 1: The loading factors are further based on the number of periods the loading factor is active for. |
| Step 9 | The System Calculates the price as the sum of the core price, Travel Residency Loading and Avocation/Hazardous Pursuits Loading. $p = p_{Core} + p_{TRL} + p_{AHP}$ Note: There maybe additional loading factors that will be used in the future. (This is most likely based on the product offering itself.) |
| Step 10 | The System calculates the fee and commissions for the current Time Period: $$c_{FeesCommissions} = p_{Core}\left(\frac{r}{1-r}\right) + f$$ |
| Step 11 | The Time Period price is calculated as a summation of the fee and commissions and the core cost: $p_{Premium} = p + c_{Fees\ Commissons}$ |
| Step 12 | Finally, the yearly premium is divided by the invoicing interval (e.g. 365.25 days in a year): $$p_{Daily} = \frac{p_{Premium}}{365.25}$$ |

A trail commission tracker (TCT) component 420 calculates and tracks commissions paid to the partners in the distribution channel, such as agents, brokers and financial advisors. Partners can view and model commission revenue flow using this tool. Commission transparency is provided using an online tool to access data within the TCT component 420.

The UA module 414 may include a coverage amount component (not shown) to calculate a new coverage amount for an insurance policy based on one or more data inputs. Additionally, the UA module 414 may include a coverage time period component (not shown) to calculate a new coverage time period for an insurance policy based on one or more data inputs.

Figure 5:
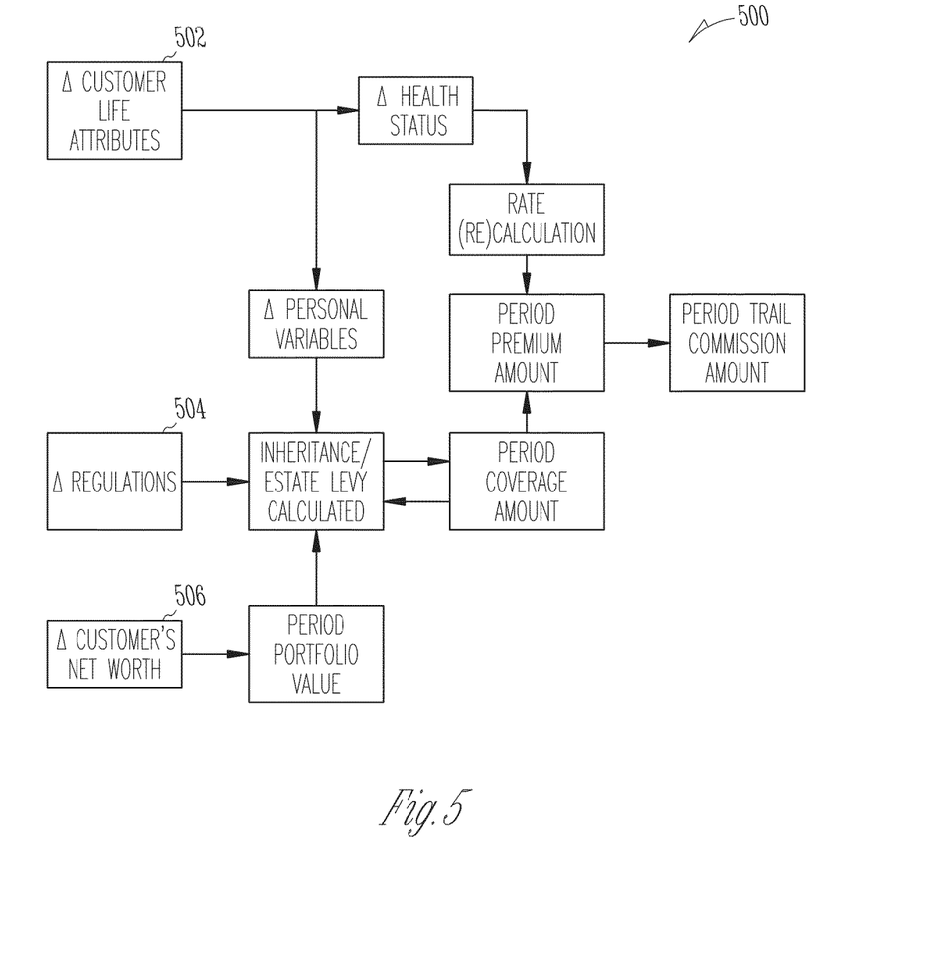
FIG. 5 is a flowchart illustrating a method, according to an example embodiment, to determine variable life protection attributes, based on dynamic inputs.

FIG. 5 is a flowchart illustrating a method 500, according to an example embodiment, to determine variable life protection attributes, based on dynamic inputs.

During a given time interval, defined by customer preference in the CI module 408, customer life attributes 502 of cholesterol and weight have increased slightly and the data are manually entered into the HW module 412. The updated cholesterol and weight data are fed into the DRA component 416 to determine if a rate recalculation is necessary. The changes in cholesterol and weight are within tolerances set by the underwriters using the DRA component 416 and the rate remains the same for the next time interval period if all other variables remained constant.

However, during the same time period the customer got married, moved to Kazakhstan, and the regulations 504 changed an inheritance tax (IHT) rate calculation. Tax deductions and exceptions for inheritance tax are automatically fed into the CI module 408. The CI module 408 assesses the new regulations 504 against the customer profile, and the changed marital status. This information, combined with regulatory changes, determines a recalculation of inheritance tax is required. The customer new tax liability is calculated.

Also during the same period, the VI module 406 identifies that the customer's net worth 506 changed, triggered by a 15% decline in the customer's stock portfolio, while the customers other assets remained unchanged. The customer's trigger threshold is set at 5% within the CI module 408 and therefore the 15% decline in stock portfolio is sufficient to trigger a request to the CI module 408 to recalculate IHT. The CI module 408 iteratively calculates the impact of the new coverage amount on IHT combined with changes in regulatory environment and marital status. A new coverage amount is either required or recommended.

The premium calculation (PC) module 418 receives a request from the CI module 408 to calculate a new period premium based on a net increase in coverage required or recommended primarily due to the customer relocating to Kazakhstan and having an increased tax liability. The PC module 418 checks with the DRA module 416 to determine if the customer's risk profile changed. In this example, the change in cholesterol and weight does not trigger a risk revaluation. The PC module 418 also checks with the UIC module 410 to determine if the increase in coverage is within the medical underwriting band. The increase in coverage is within the medical underwriting binding band and the increase in the premium does not exceed a threshold specified in the CI module 408 that would trigger the need for the customer to accept or reject the premium increase; therefore, coverage was automatically provided.

The new premium amount is calculated and the premium amount sent to the TCT module 420 to calculate and disburse trail commission payment to the customer's broker.

Modules, Components and Logic

Certain embodiments are described herein as including logic or a number of components, modules, or mechanisms. Modules may constitute either software modules (e.g., code embodied on a machine-readable storage medium or in a transmission signal) or hardware modules or devices. A device is tangible unit capable of performing certain operations and may be configured or arranged in a certain manner. In example embodiments, one or more computer systems (e.g., a standalone, client or server computer system) or one or more components of a computer system (e.g., a processor or a group of processors) may be configured by software (e.g., an application or application portion) as a device that operates to perform certain operations as described herein.

In various embodiments, a device may be implemented mechanically or electronically. For example, a device may comprise dedicated circuitry or logic that is permanently configured (e.g., as a special-purpose processor, such as a field programmable gate array (FPGA) or an application-specific integrated circuit (ASIC)) to perform certain operations. A device may also comprise programmable logic or circuitry (e.g., as encompassed within a general-purpose processor or other programmable processor) that is temporarily configured by software to perform certain operations. It will be appreciated that the decision to implement a device mechanically, in dedicated and permanently configured circuitry, or in temporarily configured circuitry (e.g., configured by software) may be driven by cost and time considerations.

Accordingly, the term "device" should be understood to encompass a tangible entity, be that an entity that is physically constructed, permanently configured (e.g., hardwired) or temporarily configured (e.g., programmed) to operate in a certain manner and/or to perform certain operations described herein. Considering embodiments in which devices are temporarily configured (e.g., programmed), each of the devices need not be configured or instantiated at any one instance in time. For example, where the devices comprise a general-purpose processor configured using software, the general-purpose processor may be configured as respective different devices at different times. Software may accordingly configure a processor, for example, to constitute a particular device at one instance of time and to constitute a different device at a different instance of time.

Devices can provide information to, and receive information from, other devices. Accordingly, the described devices may be regarded as being communicatively coupled. Where multiple of such devices exist contemporaneously, communications may be achieved through signal transmission (e.g., over appropriate circuits and buses) that connect the devices. In embodiments in which multiple devices are configured or instantiated at different times, communications between such devices may be achieved, for example, through the storage and retrieval of information in memory structures to which the multiple devices have access. For example, one device may perform an operation, and store the output of that operation in a memory device to which it is communicatively coupled. A further device may then, at a later time, access the memory device to retrieve and process the stored output. Devices may also initiate communications with input or output devices, and can operate on a resource (e.g., a collection of information).

The various operations of example methods described herein may be performed, at least partially, by one or more processors that are temporarily configured (e.g., by software) or permanently configured to perform the relevant operations. Whether temporarily or permanently configured, such processors may constitute processor-implemented modules or devices that operate to perform one or more operations or functions. The modules referred to herein may, in some example embodiments, comprise processor-implemented modules or devices.

Similarly, the methods described herein may be at least partially processor-implemented. For example, at least some of the operations of a method may be performed by one or processors or processor-implemented modules or devices. The performance of certain of the operations may be distributed among the one or more processors, not only residing within a single machine, but deployed across a number of machines. In some example embodiments, the processor or processors may be located in a single location (e.g., within a home environment, an office environment or as a server farm), while in other embodiments the processors may be distributed across a number of locations.

The one or more processors may also operate to support performance of the relevant operations in a "cloud computing" environment or as a "software as a service" (SaaS). For example, at least some of the operations may be performed by a group of computers (as examples of machines including processors), these operations being accessible via a network (e.g., the Internet) and via one or more appropriate interfaces (e.g., Application Program Interfaces (APIs).)

Electronic Apparatus and System

Example embodiments may be implemented in digital electronic circuitry, or in computer hardware, firmware, software, or in combinations of them. Example embodiments may be implemented using a computer program product, e.g., a computer program tangibly embodied in an information carrier, e.g., in a machine-readable storage medium for execution by, or to control the operation of, data processing apparatus, e.g., a programmable processor, a computer, or multiple computers.

A computer program can be written in any form of programming language, including compiled or interpreted languages, and it can be deployed in any form, including as a stand-alone program or as a module, subroutine, or other unit suitable for use in a computing environment. A computer program can be deployed to be executed on one computer or on multiple computers at one site or distributed across multiple sites and interconnected by a communication network.

In example embodiments, operations may be performed by one or more programmable processors executing a computer program to perform functions by operating on input data and generating output. Method operations can also be performed by, and apparatus of example embodiments may be implemented as, special purpose logic circuitry, e.g., a field programmable gate array (FPGA) or an application-specific integrated circuit (ASIC).

The computing system can include clients and servers. A client and server are generally remote from each other and typically interact through a communication network. The relationship of client and server arises by virtue of computer programs running on the respective computers and having a client-server relationship to each other. In embodiments deploying a programmable computing system, it will be appreciated that that both hardware and software architectures require consideration. Specifically, it will be appreciated that the choice of whether to implement certain functionality in permanently configured hardware (e.g., an ASIC), in temporarily configured hardware (e.g., a combination of software and a programmable processor), or a combination of permanently and temporarily configured hardware may be a design choice. Below are set out hardware (e.g., machine) and software architectures that may be deployed, in various example embodiments.

Example Machine Architecture and Machine-Readable Storage Medium

Figure 6:
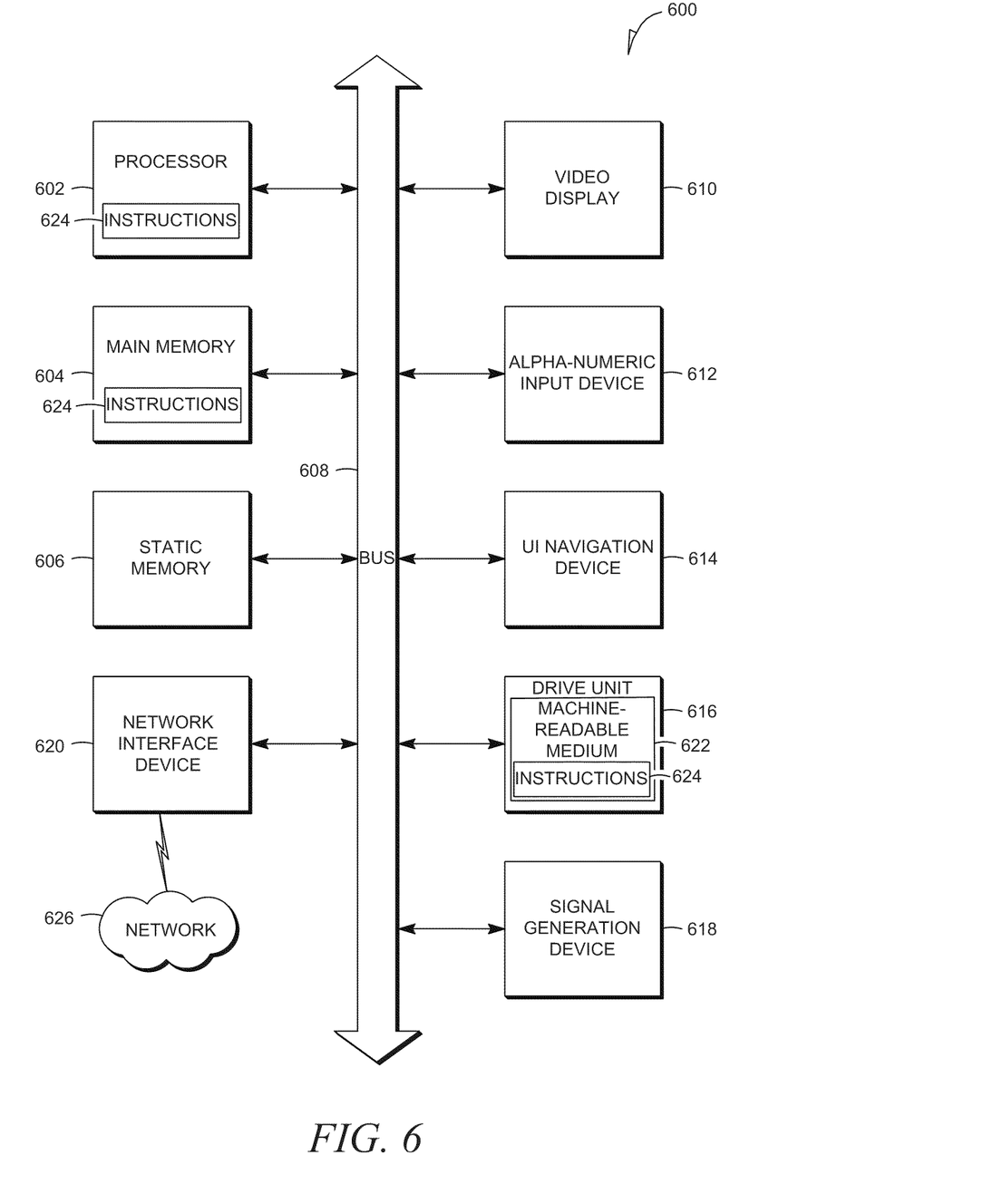
FIG. 6 is a block diagram of machine in the example form of a computer system within which instructions, for causing the machine to perform any one or more of the methodologies discussed herein, may be executed.

FIG. 6 is a block diagram of machine in the example form of a computer system 600 within which instructions, for causing the machine to perform any one or more of the methodologies discussed herein, may be executed. In alternative embodiments, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a personal computer (PC), a tablet PC, a set-top box (STB), a Personal Digital Assistant (PDA), a cellular telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 600 includes a processor 602 (e.g., a central processing unit (CPU), a graphics processing unit (GPU) or both), a main memory 604 and a static memory 606, which communicate with each other via a bus 608. The computer system 600 may further include a video display unit 610 (e.g., a liquid crystal display (LCD) or a cathode ray tube (CRT)). The computer system 600 also includes an alphanumeric input device 612 (e.g., a keyboard), a user interface (UI) navigation device 614 (e.g., a mouse), a disk drive unit 616, a signal generation device 618 (e.g., a speaker) and a network interface device 620.

Machine-Readable Storage Medium

The disk drive unit 616 includes a machine-readable storage medium 622 on which is stored one or more sets of instructions and data structures (e.g., software) 624 embodying or utilized by any one or more of the methodologies or functions described herein. The instructions 624 may also reside, completely or at least partially, within the main memory 604 and/or within the processor 602 during execution thereof by the computer system 600, the main memory 604 and the processor 602 also constituting machine-readable media.

While the machine-readable storage medium 622 is shown in an example embodiment to be a single medium, the term "machine-readable storage medium" may include a single medium or multiple media (e.g., a centralized or distributed database, and/or associated caches and servers) that store the one or more instructions or data structures. The term "machine-readable storage medium" shall also be taken to include any tangible medium that is capable of storing, encoding or carrying instructions for execution by the machine and that cause the machine to perform any one or more of the methodologies of the present invention, or that is capable of storing, encoding or carrying data structures utilized by or associated with such instructions. The term "machine-readable storage medium" shall accordingly be taken to include, but not be limited to, solid-state memories, and optical and magnetic media. Specific examples of machine-readable storage media include non-volatile memory, including by way of example semiconductor memory devices, e.g., Erasable Programmable Read-Only Memory (EPROM), Electrically Erasable Programmable Read-Only Memory (EEPROM), and flash memory devices; magnetic disks such as internal hard disks and removable disks; magneto-optical disks; and CD-ROM and DVD-ROM disks.

Transmission Medium

The instructions 624 may further be transmitted or received over a communications network 626 using a transmission medium. The instructions 624 may be transmitted using the network interface device 620 and any one of a number of well-known transfer protocols (e.g., HTTP). Examples of communication networks include a local area network ("LAN"), a wide area network ("WAN"), the Internet, mobile telephone networks, Plain Old Telephone (POTS) networks, and wireless data networks (e.g., WiFi and WiMax networks). The term "transmission medium" shall be taken to include any intangible medium that is capable of storing, encoding or carrying instructions for execution by the machine, and includes digital or analog communications signals or other intangible media to facilitate communication of such software.

Although an embodiment has been described with reference to specific example embodiments, it will be evident that various modifications and changes may be made to these embodiments without departing from the broader spirit and scope of the invention. Accordingly, the specification and drawings are to be regarded in an illustrative rather than a restrictive sense. The accompanying drawings that form a part hereof, show by way of illustration, and not of limitation, specific embodiments in which the subject matter may be practiced. The embodiments illustrated are described in sufficient detail to enable those skilled in the art to practice the teachings disclosed herein. Other embodiments may be utilized and derived therefrom, such that structural and logical substitutions and changes may be made without departing from the scope of this disclosure. This Detailed Description, therefore, is not to be taken in a limiting sense, and the scope of various embodiments is defined only by the appended claims, along with the full range of equivalents to which such claims are entitled.

What is claimed is:

1. A method comprising:
    automatically adjusting a face amount of an existing insurance policy generated by a dynamic provisioning system and stored in a database of the dynamic provisioning system, the adjusting based on preferences of an entity associated with the existing insurance policy, the preferences including a time period and trigger thresholds for input data items, the trigger thresholds specifying when the input data items are considered for automatic recalculation of underwriting risk associated with the insurance policy in real-time when the input data items are received in automatic data feeds at the dynamic provisioning system, the automatic adjusting comprising:
    establishing one or more communication channels between one or more biometric sensors and one or more third-party systems connected to the dynamic provisioning system, wherein the one or more third-party systems include a user system associated with the entity;
    receiving the preferences at the dynamic provisioning system via the one or more communication channels;
    receiving automatic data feeds at the dynamic provisioning system via the one or more communication channels, the automatic data feeds initiated by the dynamic provisioning system periodically to receive the input data items, which include biometric data received from the one or more biometric sensors;
    based on the receiving of the input data items being within the time period and a determining that at least one of the input data item exceeds at least one of the trigger thresholds, performing operations in real-time, the operations including:
    performing the recalculation of the underwriting risk;
    determining a recommended coverage amount for the existing insurance policy based on the recalculation of the underwriting risk;
    automatically adjusting the face amount of the existing insurance policy to correspond to the recommended coverage amount based on a determining that the recommended coverage amount falls within a binding band of the existing insurance policy, the automatic adjusting including generating an amended insurance policy for storing in the database of the dynamic provisioning system, the automatic adjusting being performed without triggering a request for the entity to accept or reject the automatic adjusting via a user interface of the user system, one or more modules incorporated into the dynamic provisioning system to perform the receiving of the preferences, the receiving of the automatic data feeds, the performing of the recalculation of the recommended coverage amount, the automatic adjusting of the face amount, the one or more modules implemented by one or more processors of the dynamic provisioning system, the one or more modules including instructions stored in a non-transitory machine-readable storage medium.

2. The method of claim 1, wherein the input data items include at least one of an entity input data item and an environmental input data item, the entity input data item being specific to the entity and the environmental input data not being specific to the entity.

3. The method of claim 1, wherein at least one of the third-party systems is a financial data system and the data input data items are captured via an Internet-based portfolio administration service.

4. A system comprising:
    one or more modules incorporated into a dynamic provisioning system, the one or more modules implemented by one or more processors of the dynamic provisioning system, the one or more modules including instructions stored in a non-transitory machine-readable storage medium, the one or more modules configured to, at least:
    establishing one or more communication channels between one or more biometric sensors and one or more third-party systems connected to the dynamic provisioning system, wherein the one or more third-party systems include a user system associated with an entity, the entity associated with an existing insurance policy generated by the dynamic provisioning system and stored in a database of the dynamic provisioning system;
    receive preferences of the entity at the dynamic provisioning system via the one or more communication channels, the preferences including a time period and trigger thresholds for input data items, the trigger thresholds specifying when the input data items are considered for recalculation of underwriting risk associated with the insurance policy;
    receive automatic data feeds at the dynamic provisioning system via the one or more communication channels, the automatic data feeds initiated by the dynamic provisioning system periodically to receive the input data items, the input data items including biometric data received from the one or more biometric sensors;
    based on the receiving of the input data items being within the time period and a determining that at least one of the input data item exceeds at least one of the trigger thresholds, performing operations in real time, the operations including:
    performing the recalculation of the underwriting risk;
    determining a recommended coverage amount for the existing insurance policy based on the recalculation of the underwriting risk;
    automatically adjusting a face amount of the existing insurance policy to correspond to the recommended coverage amount based on a determining that the recommended coverage amount falls within a binding band of the existing insurance policy, the automatic adjusting including generating an amended insurance policy for storing in the database of the dynamic provisioning system, the automatic adjusting being performed without triggering a request for the entity to accept or reject the automatic adjusting via a user interface of the user system.

5. The system of claim 4, wherein the input data items include at least one of an entity input data item and an environmental input data item, the entity input data item being specific to the entity and the environmental input data not being specific to the entity.

6. The system of claim 4, wherein at least one of the third-party systems is a financial data system and the data input data items are captured via an Internet-based portfolio administration service.

7. A non-transitory machine-readable storage medium comprising instructions that, when incorporated as one or more modules into a dynamic provisioning system, cause the one or more processors of the dynamic provisioning system to perform operations, the operations comprising:

establishing one or more communication channels between one or more biometric sensors and one or more third-party systems connected to the dynamic provisioning system, wherein the one or more third-party systems include a user system associated with an entity;

receiving preferences of the entity associated with an existing insurance policy via the one or more communication channels, the existing insurance policy generated by the dynamic provisioning system and stored in a database of the dynamic provisioning system, the preferences including a time period and trigger thresholds for input data items, the trigger thresholds specifying when the input data items are considered for recalculation of underwriting risk associated with the insurance policy;

receiving automatic data feeds at the dynamic provisioning system from the one or more via the one or more communication channels, the automatic data feeds initiated by the dynamic provisioning system periodically to receive the input data items, the input data items including biometric data received from the one or more biometric sensors;

based on the receiving of the input data items being within the time period and a determining that at least one of the input data item exceeds at least one of the trigger thresholds, performing additional operations in real-time, the additional operations including:

performing the recalculation of the underwriting risk;

determining a recommended coverage amount for the existing insurance policy based on the recalculation of the underwriting risk;

automatically adjusting a face amount of the existing insurance policy to correspond to the recommended coverage amount based on a determining that the recommended coverage amount falls within a binding band of the existing insurance policy, the automatic adjusting including generating an amended insurance policy for storing in the database of the dynamic provisioning system, the automatic adjusting being performed without triggering a request for the entity to accept or reject the automatic adjusting via a user interface of the user system.

8. The non-transitory machine-readable storage medium of claim 7, wherein the input data items include at least one of an entity input data item and an environmental input data item, the entity input data item being specific to the entity and the environmental input data not being specific to the entity.

9. The method of claim 1, wherein the adjusting of the face amount of the existing insurance policy is based on a level of verifiability of the entity input data items transgressing a threshold.

10. The method of claim 1, further comprising:
receiving additional input data items;
determining a weighted input data item based on a level of verifiability of the input data item;
determining a weighted additional input data item based on a level of verifiability of the additional input data item; and
wherein the determining of the recommended coverage amount is based on the weighted input data item and the weighted additional input data item.

11. The method of claim 1, wherein the input data item pertains to a net worth of the entity.

12. The method of claim 1, wherein the input data item pertains to an inheritance tax rate of the entity.

13. The method of claim 1, wherein the third-party systems include one or more regulatory computer systems, medical data systems, and financial data systems.

14. The method of claim 13, wherein at least a subset of the input data items is associated with the financial data systems and includes an investment portfolio data of the entity and market data pertaining to the investment portfolio.

15. The method of claim 13, wherein at least a subset of the input data items is associated with the regulatory computer system and includes information pertaining to changes in inheritance tax rates or estate tax rates with respect to the entity.

16. The method of claim 13, wherein at least a subset of the input data items is associated with the medical data systems and includes at least one biometric input received automatically through a biometric device, the biometric input including a sensed physiological characteristic of the entity.

17. The method of claim 13, wherein at least a subset of the input data items is associated with the medical data systems and includes at least of one independently-verified input data item pertaining to the entity's EKG, weight, BMI, or cholesterol measurements.

18. The method of claim 13, wherein at least one of the automatic data feeds includes information collected in real-time on the user system, the information including a location of the user system.

* * * * *